United States Patent [19]

Ohashi et al.

[11] Patent Number: 5,683,883
[45] Date of Patent: Nov. 4, 1997

[54] **OLIGONUCLEOTIDES FOR DETECTING *SALMONELLA* SPECIES AND DETECTION PROCESS USING THE SAME**

[75] Inventors: Tetsuo Ohashi, Uji; Reiko Tanaka, Kyoto, both of Japan

[73] Assignee: Shimadzu Corporation, Kyoto, Japan

[21] Appl. No.: 637,902

[22] Filed: Apr. 26, 1996

[30] Foreign Application Priority Data

Apr. 28, 1995 [JP] Japan .................................. 7-105192

[51] Int. Cl.$^6$ .............................. C12Q 1/68; C12P 19/34; C07H 19/00; C07H 21/02
[52] U.S. Cl. .................. 435/6; 536/22.1; 536/23.1; 536/24.3; 536/25.3; 435/91.1; 435/91.2
[58] Field of Search .................... 536/22.1, 23.1, 536/24.3, 25.3; 435/6, 91.1, 91.2

[56] References Cited

U.S. PATENT DOCUMENTS 5,089,386 2/1992 Stackebrandt et al. ................. 435/6

OTHER PUBLICATIONS

Chopra et al. "Cloning and sequence of hydrogenase regulatory genes (hydHG) from *Salmonella typhimurium*", Biochemica et Blophysica Acta vol. 11229, pp.115–118, 1991.

Galan et al. "Molecular and Functional Characterization of the Salmonella Invasion Gene invA: Homology of InvA to Members of a New Protein Family" Journal of Bacteriology, vol. 1734, No. 13, pp. 4338–4349, Jul. 1992.

Chopra et al. "Molecular characterization of an enterotoxin from *Salmonella tiphymurium*" Microb. Pathog. vol. 16, pp.85–98, 1994.

*Primary Examiner*—Ardin H. Marschel
*Assistant Examiner*—Jezia Riley

[57] ABSTRACT

Synthetic oligonucleotides having a nucleotide sequence contained in the enterotoxin genes of Salmonella species; a method for detecting a bacterial strain of Salmonella species in test specimens by amplifying a region of the genes by PCR using the above oligonucleotides as primers; and a kit for the detection of Salmonella species.

13 Claims, No Drawings

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear (i i) MOLECULE TYPE: genomic DNA (i i i) HYPOTHETICAL: NO (i v) ANTI-SENSE: NO (v i) ORIGINAL SOURCE:
    (A) ORGANISM: Salmonella typhimurium (i x) FEATURE:
    (C) IDENTIFICATION METHOD: S (x i) SEQUENCE DESCRIPTION: SEQ ID NO:1:

CTTTGGTCGT AAAATAAGGC G      21

(2) INFORMATION FOR SEQ ID NO:2:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (i i) MOLECULE TYPE: genomic DNA (i i i) HYPOTHETICAL: NO (i v) ANTI-SENSE: NO (v i) ORIGINAL SOURCE:
        (A) ORGANISM: Salmonella typhimurium (i x) FEATURE:
        (C) IDENTIFICATION METHOD: S (x i) SEQUENCE DESCRIPTION: SEQ ID NO:2:

GAATCTCTCT GCTTTGGGCA      20

(2) INFORMATION FOR SEQ ID NO:3:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (i i) MOLECULE TYPE: genomic DNA (i i i) HYPOTHETICAL: NO (i v) ANTI-SENSE: NO (v i) ORIGINAL SOURCE:
        (A) ORGANISM: Salmonella typhimurium (i x) FEATURE:
        (C) IDENTIFICATION METHOD: S (x i) SEQUENCE DESCRIPTION: SEQ ID NO:3:

AGCTTTGGTC GTAAAATAAG G      21

(2) INFORMATION FOR SEQ ID NO:4:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (i i) MOLECULE TYPE: genomic DNA (i i i) HYPOTHETICAL: NO ( i v ) ANTI-SENSE: NO ( v i ) ORIGINAL SOURCE:
                    ( A ) ORGANISM: Salmonella typhimurium ( i x ) FEATURE:
                    ( C ) IDENTIFICATION METHOD: S ( x i ) SEQUENCE DESCRIPTION: SEQ ID NO:4:

TGCCCAAAGC AGAGAGATTC                                                                                    20

( 2 ) INFORMATION FOR SEQ ID NO:5:

( i ) SEQUENCE CHARACTERISTICS:
                    ( A ) LENGTH: 20 base pairs
                    ( B ) TYPE: nucleic acid
                    ( C ) STRANDEDNESS: single
                    ( D ) TOPOLOGY: linear ( i i ) MOLECULE TYPE: genomic DNA ( i i i ) HYPOTHETICAL: NO ( i v ) ANTI-SENSE: NO ( v i ) ORIGINAL SOURCE:
                    ( A ) ORGANISM: Salmonella typhimurium ( i x ) FEATURE:
                    ( C ) IDENTIFICATION METHOD: S ( x i ) SEQUENCE DESCRIPTION: SEQ ID NO:5:

CAAAGGGCTG GCGAAATACT                                                                                    20

( 2 ) INFORMATION FOR SEQ ID NO:6:

( i ) SEQUENCE CHARACTERISTICS:
                    ( A ) LENGTH: 20 base pairs
                    ( B ) TYPE: nucleic acid
                    ( C ) STRANDEDNESS: single
                    ( D ) TOPOLOGY: linear ( i i ) MOLECULE TYPE: genomic DNA ( i i i ) HYPOTHETICAL: NO ( i v ) ANTI-SENSE: NO ( v i ) ORIGINAL SOURCE:
                    ( A ) ORGANISM: Salmonella typhimurium ( i x ) FEATURE:
                    ( C ) IDENTIFICATION METHOD: S ( x i ) SEQUENCE DESCRIPTION: SEQ ID NO:6:

GATGCCCAAA GCAGAGAGAT                                                                                    20

( 2 ) INFORMATION FOR SEQ ID NO:7:

( i ) SEQUENCE CHARACTERISTICS:
                    ( A ) LENGTH: 20 base pairs
                    ( B ) TYPE: nucleic acid
                    ( C ) STRANDEDNESS: single
                    ( D ) TOPOLOGY: linear ( i i ) MOLECULE TYPE: genomic DNA ( i i i ) HYPOTHETICAL: NO ( i v ) ANTI-SENSE: NO ( v i ) ORIGINAL SOURCE:
                    ( A ) ORGANISM: Salmonella typhimurium

```
        ( i x ) FEATURE:
                ( C ) IDENTIFICATION METHOD: S ( x i ) SEQUENCE DESCRIPTION: SEQ ID NO:7:

GGGTCGTTCT ACATTGACAG                                                                    20

( 2 ) INFORMATION FOR SEQ ID NO:8:

( i ) SEQUENCE CHARACTERISTICS:
                ( A ) LENGTH: 20 base pairs
                ( B ) TYPE: nucleic acid
                ( C ) STRANDEDNESS: single
                ( D ) TOPOLOGY: linear ( i i ) MOLECULE TYPE: genomic DNA ( i i i ) HYPOTHETICAL: NO ( i v ) ANTI-SENSE: NO ( v i ) ORIGINAL SOURCE:
                ( A ) ORGANISM: Salmonella typhimurium ( i x ) FEATURE:
                ( C ) IDENTIFICATION METHOD: S ( x i ) SEQUENCE DESCRIPTION: SEQ ID NO:8:

TTCCCTTTCC AGTACGCTTC                                                                    20

( 2 ) INFORMATION FOR SEQ ID NO:9:

( i ) SEQUENCE CHARACTERISTICS:
                ( A ) LENGTH: 20 base pairs
                ( B ) TYPE: nucleic acid
                ( C ) STRANDEDNESS: single
                ( D ) TOPOLOGY: linear ( i i ) MOLECULE TYPE: genomic DNA ( i i i ) HYPOTHETICAL: NO ( i v ) ANTI-SENSE: NO ( v i ) ORIGINAL SOURCE:
                ( A ) ORGANISM: Salmonella typhimurium ( i x ) FEATURE:
                ( C ) IDENTIFICATION METHOD: S ( x i ) SEQUENCE DESCRIPTION: SEQ ID NO:9:

CATCCGCATC AATAATACCG                                                                    20
```

OLIGONUCLEOTIDES FOR DETECTING *SALMONELLA* SPECIES AND DETECTION PROCESS USING THE SAME

BACKGROUND OF THE INVENTION

1. Field of the Invention

The present invention relates to detection of Salmonella species causative of food poisoning in clinical tests or food inspections.

2. Discussion of the Related Art

The specimens tested for food poisoning are collected from the materials in the surroundings of patients, such as patient's excreta or feces, food and wiping materials. Detection and identification of Salmonella species with these specimens conventionally require to perform enrichment culture, confirmation culture and antigen determination (serotyping). The bacteria of Salmonella species are divided into many serotypes, and complete serotyping requires as many as 100 antisera and much experience, thereby making it difficult to carry out the detection of Salmonella species in an ordinary laboratory. Also, each culture step takes 18 to 24 hours, and as a whole it takes about 3 days from enrichment culture to serotyping. Thus, the method described above is poor in rapidity. Furthermore, confirmation culture involves inoculation of bacteria to TSI agar, SIM medium, VP-MR medium and lysine decarboxylation test medium, and subsequent overnight culture at 37° C.; the serotyping needs the use of commercially available set of antisera against O and H antigens; these operations make the detection tedious and costly.

In recent years, DNA probing or hybridization using oligonucleotides has been tried for the detection of bacteria. However, when hybridization of a labeled oligonucleotide probe is carried out on a membrane or on other supports, the sensitivity depends on the number of organisms available for the detection. Therefore, without the above-described cultures as pretreatments, it is difficult to achieve high sensitivity and high selectivity in detecting the bacteria of interest.

SUMMARY OF THE INVENTION

It is an object of the present invention to provide synthetic oligonucleotides used as primers for PCR to amplify the enterotoxin genes specific to Salmonella species.

It is another object of the present invention to provide a simple, rapid and highly sensitive process for detecting the enterotoxin genes specific to Salmonella species for quarantine inspection of food poisoning and clinical laboratory tests for diarrheal patients.

DETAILED DESCRIPTION OF THE INVENTION

The main feature of the present invention resides in a process of selectively amplifying a DNA sequence contained in an enterotoxin gene of Salmonella species causative of food poisoning by the PCR technique, using oligonucleotide primers chemically synthesized to specifically hybridize with the gene; and then detecting the amplified gene sequence.

According to the present invention, a high selectivity and sensitivity can be achieved in the detection of enterotoxic Salmonella species using the PCR technique.

Because of high sensitivity, the detection of the present invention does not require a large amount of specimens nor complicated pretreatments of specimens. Also, the present method can significantly reduce the time needed for the detection because of short reaction time, simple equipment, and easy operation. Actually, in the examples of the present application, it took only about 3.5 hours for the entire detection, i.e., 3 hours for amplification and 0.5 hours for detection.

By the use of agarose gel electrophoresis and nucleic acid staining with ethidium bromide in the detection of the present invention, a label-free oligonucleotide probe can be used and the length of DNA fragment can be confirmed, thereby making the detection highly reliable.

The present method can detect all the Salmonella species causative of food poisoning, regardless of species and serotypes. Thus, as compared with the method for individually detecting different species and serotypes, the present invention can provide extremely useful reagents and methods for the detection of Salmonella species.

Oligonucleotides

When the stn gene, an enterotoxin gene of *Salmonella typhimurium*, is targeted, the following oligonucleotide primers that are complementary to the gene are chemically synthesized: Oligonucleotides of SEQ ID NOS: 1 to 6 and oligonucleotides complementary thereto.

When the inv A gene, another enterotoxin gene of *Salmonella typhimurium*, is targeted, the following oligonucleotide primers that are complementary to the gene are chemically synthesized: Oligonucleotides of SEQ ID NOS: 7 to 9 and oligonucleotides complementary thereto.

Amplification of Gene Sequence by PCR

For amplification of a region of a target gene in the present invention, the PCR developed by Saiki et al. [Science 230, 1350 (1985)] is employed.

Specifically, two oligonucleotide primers that flank a nucleotide sequence of interest, i.e., the enterotoxin genes of Salmonella species in the present invention, are synthesized. One of the oligonucleotide primers selectively hybridizes to the (+)-strand of a target gene, and the other hybridizes to the (−)-strand of the gene. Then, both the oligonucleotides serve as primers of template dependent DNA polymerization. Each of the single strands of the target DNA resulting from heat denaturation of the double stranded DNA in specimens serves as the template. The duplexes formed by the DNA polymerization reaction are then denatured to separate the primer extension products from the templates. Then, the primer extension products themselves serve as the templates for the next DNA polymerization reaction. The cycle of denaturation, primer annealing (hybridization of primers to the template DNAs) and primer extension reaction is repeated until the region flanked by the two primers is amplified to a detectable level.

Specimens applicable to the PCR in the present invention may include clinical samples, such as feces, urine, blood, tissue homogenate, and food samples. A specimen for PCR should be pre-treated to release the nucleic acid components from the bacterial cells present therein. Since PCR can proceed with only several to several tens of nucleic acid molecules, a test solution containing an adequate amount of nucleic acid can be prepared simply by treating a specimen for a short time with a lyric enzyme, a surfactant or an alkali.

The oligonucleotides used as primers in the present invention may be either synthetic or natural, and in view of selectivity, detection sensitivity and reproducibility, their length is not less than 10 bases, preferably not less than 15 bases. It is not necessary to label the primers for detection.

The region to be amplified in a target gene, i.e., the stn gene or the inv A gene of Salmonella species, is 50 to 2000 bp in length, preferably 100 to 1000 bp.

As the agent for polymerization, a thermostable DNA polymerase is used. The sources from which the enzyme is derived are not particularly limited as long as the enzyme retains its activity at temperatures of from 90° to 95° C. The denaturation is carried out at a temperature of from 90° to 95° C.; the primer annealing, from 37° to 65° C.; and the polymerization reaction, from 50° to 75° C. The cycle of denaturation, primer annealing, and polymerization is repeated 20 to 42 times.

The presence or absence and the length of the amplified DNA fragment can be detected by subjecting the reaction solution to agarose gel electrophoresis after the completion of PCR. Other types of electrophoresis and chromatography can also be used for the detection.

The presence of a nucleotide sequence of a Salmonella enterotoxin gene in a specimen indicates that the specimen is positive for the Salmonella species.

In the detection of a target DNA on a membrane or other supports, one of the oligonucleotide primers (SEQ ID NOS: 1 to 9) may be used as a probe. In this case, it is preferable to label the oligonucleotide.

The following examples are offered by way of illustration and are not intended to limit the invention in any manner.

EXAMPLES

Example 1

Detection of the stn Gene of Salmonella Species (*Salmonella typhimurium*)

[Experiment 1]

Preparation of specimens

The 174 strains of Salmonella species listed in Tables 1-1 to 1-7 were obtained from specimens in food poisoning cases, e.g., diarrheal feces and vomit of patients, and causative food of food poisoning. Each strain was inoculated to a Brain Heart Infusion medium (manufactured by BBL), and subjected to overnight shaking culture at 37° C. under aerobic conditions. Each culture broth was diluted with 10 mM Tris-HCl buffer, pH 7.5 (hereinafter referred to as TE buffer), and heated at 95° C. for 10 minutes, and subjected to centrifugation. The supernatant was used as a specimen.

Synthesis of Primers

As the primers for amplifying the stn gene of *Salmonella typhimurium*, the oligonucleotide sequences set forth in the Sequence Listing (SEQ ID NOS: 1 to 6) were selected based upon the known nucleotide sequence of the stn gene (Chopra, A. K. et al., Microbial Pathogenesis 16, 85–98 (1994)). The oligonucleotide primers were chemically synthesized by the β-cyanoethylphosphoamidite method using a Cyclone Plus DNA synthesizer (manufactured by MilliGen/Bioresearch). The synthesized oligonucleotides were purified by high performance liquid chromatography using a C18 reversed-phase column.

PCR

To 3 µl of the specimen as prepared above, 16.05 µl of sterile distilled water, 3 µl of 10× reaction buffer, 4.8 µl of dNTP solution, 1.5 µl each of primer (A) and primer (B), and 0.15 µl of a thermostable DNA polymerase were added to make 30 µl of a reaction mixture. On the reaction mixture, 50 µl of mineral oil (produced by SIGMA) was overlaid.

Reaction Mixture for PCR

10× reaction buffer: 500 mM KCl, 100 mM Tris-HCl, pH 8.3, 15 mM $MgCl_2$, 0.1% (w/v) gelatin.

dNTP solution: A mixture of dATP, dCTP, dGTP and dTTP, each having a final concentration of 1.25 mM.

Primers (A) and (B): Aqueous solution of the above-described chemically synthesized and purified oligonucleotides (concentration, 3.75 OD/ml).

The oligonucleotide primers synthesized were used in the following combinations:

| Primer (A) | Primer (B) |
| --- | --- |
| SEQ ID NO:1 | SEQ ID NO:4 |
| SEQ ID NO:2 | SEQ ID NO:5 |
| SEQ ID NO:3 | SEQ ID NO:6 |

Thermostable DNA polymerase: Taq DNA polymerase (5 unit/ml; produced by Perkin Elmer Cetus).

Reaction conditions

Denaturation: 94° C., 1 minute.

Annealing: 55° C., 1 minute.

Elongation: 72° C., 1 minute.

The cycle of denaturation, primer annealing and elongation (5.7 minutes) was repeated 35 times (entire time, about 3 hours). This procedure was performed using a DNA thermal cycler (produced by Perkin Elmer Cetus) in which the above reaction conditions had been programmed.

Detection

Agarose Gel Electrophoresis

Agarose gel electrophoresis was employed to detect the amplified DNA.

The reaction mixture after the PCR thermal cycling was applied to a 3% (w/v) agarose gel and separated by electrophoresis at a constant voltage of 100V for 30 minutes. A 0.5 µg/ml ethidium bromide solution was used as a fluorescent dye to detect the DNA bands. Operation procedures and other conditions employed are described by Maniatis et al. (Molecular Cloning, 2nd edition (1989)). In addition to the reaction mixture, a molecular weight marker was also electrophoresed concurrently. The length of the DNA fragment was calculated by comparing the relative mobilities.

Results

The nucleotide sequence of the stn gene of *Salmonella typhimurium* is known. Since the complementary sequence to part of the hyd G gene, or the hyd H gene), an essential enzyme for Salmonella species, the DNA sequence of the stn gene is thought to be common to all Salmonella species. The length of the nucleotide fragment amplified by PCR using the oligonucleotide primers of the present invention can easily be estimated.

Specifically, when oligonucleotides of SEQ ID NO: 1 and SEQ ID NO: 4 are used in combination, the length of the DNA fragment amplified is estimated to be 260 bp. Similarly, the combination of SEQ ID NO: 2 and SEQ ID NO: 5 and that of SEQ ID NO: 3 and SEQ ID NO: 6 amplify DNA fragment of 224 bp and that of 264 bp, respectively. When the estimation accorded with the length of the DNA fragment actually amplified, the combination of primers was evaluated to accurately amplify the target nucleotide sequence in the stn gene and marked with "+" as shown in Tables 1-1 to 1-7, whereas the combination of primers that failed to amplify the target nucleotide sequence was marked with "−" in the Tables. As obvious from Tables 1-1 to 1-7, the stn gene was accurately amplified in all the Salmonella species tested.

[Experiment 2]

To determine whether the results obtained in Experiment 1 are specific to Salmonella species having the stn gene, the genes of clinically important enterotoxic bacteria other than Salmonella species were examined with the oligonucleotide primers of the present invention. In particular, differentiation between Salmonella species and Citrobacter species, which is difficult by conventional methods, was carefully examined.

Preparation of Specimens

The test strains are listed in Tables 2-1 to 2-12. The same procedure as used in Experiment 1 was carried out, except for the following changes in conditions: *Clostridium perfringens*, *Campylobacter jejuni*, *Campylobacter coli*, *Bacteroides flagilis*, *Bacteroides vulgatus*, *Lactobacillus acidophilus*, and *Bifidobacterium adolescentis* were cultured at 37° C. under anaerobic conditions, while *Neisseria gonorrhoeae* and *Neisseria meningitidis* were cultured in the presence of 3–10% $CO_2$. Human placenta DNA, at a concentration of 1 μg/ml, was also subjected to PCR in the same manner as above.

Results

The results are shown in Tables 2-1 to 2-12. The combinations of the oligonucleotide primers of the present invention did not amplify any DNA fragments of other bacterial strains than Salmonella species nor human placenta DNA. It is of particular importance that though there were a very few exceptions, the combinations of the primers of the present invention did not amplify DNAs of Citrobacter species, which are closely akin to and hardly differentiated from Salmonella species, with 93% or higher accuracy. It can therefore be concluded that the oligonucleotide primers of the present invention react with the DNAs of Salmonella species with high selectivity, thereby giving a highly reliable results.

The agarose gel electrophoresis used in the above experiments can differentiate DNA fragments which are different in length by 5–10 bp for DNA fragments of not less than 100 bp and by 10–20 for DNA fragments of 100–500 bp. In addition, the use of other gel material such as acrylamide can improve the precision of the measurement of the length of DNA fragment, thereby further increasing the reliability of the specific detection of the stn gene.

Example 2

Detection of the inv A gene of Salmonella species

[Experiment 1]

Preparation of Specimens

The test specimens were prepared as described in Example 1.

Synthesis of Primers

As primers for amplifying the inv A gene of Salmonella species, the oligonucleotides of SEQ ID NOS: 7 to 9 set forth in the Sequence Listing were selected based upon the known nucleotide sequence of the inv A gene (Galan, J. E. et al., J. Bacteriol. 174, 4338–4349 (1992)). The oligonucleotide primers were chemically synthesized and purified in the same way as described in Example 1.

PCR

The same procedures and conditions as those in Example 1 were used except that the following combinations of primers were employed:

| Primer (A) | Primer (B) |
|---|---|
| SEQ ID NO:7 | SEQ ID NO:8 |
| SEQ ID NO:7 | SEQ ID NO:9 |

Detection

The same procedures as in Example 1 were followed.

Results

The nucleotide sequence of the inv A gene of Salmonella species is known. Therefore, the length of the DNA fragment amplified by PCR using the oligonucleotide primers of the present invention can easily be estimated.

When oligonucleotides of SEQ ID NO: 7 and SEQ ID NO: 8 are used in combination, the length of the DNA fragment amplified is estimated to be 378 bp. Similarly, the combination of SEQ ID NO: 7 and SEQ ID NO: 9 amplifies a DNA fragment of 343 bp.

When the estimation accorded with the length of the DNA fragment actually amplified, the combination of primers was evaluated to accurately amplify the target nucleotide sequence in the inv A gene and marked with "+" as shown in Tables 1-1 to 1-7, whereas the combination of primers that failed to amplify the target nucleotide sequence was marked with "−" in the Tables. As obvious from Tables 1-1 to 1-7, the inv gene was accurately amplified for all the Salmonella species tested.

[Experiment 2]

To determine whether the results obtained in Experiment 1 are specific to Salmonella species having the inv A gene, the genes of clinically important enterotoxic bacteria other than Salmonella species were examined with the oligonucleotide primers of the present invention in the same manner as in Example 1.

The results are shown in Tables 2-1 to 2-12. The combinations of the oligonucleotide primers of the present invention did not amplify any nucleotide fragments derived from other enterotoxic bacterial strains nor other sources. It can therefore be concluded that the oligonucleotide primers of the present invention react with the DNAs of Salmonella species with high selectivity, thereby giving a highly reliable detection results.

While the invention has been described in detail with reference to specific embodiments thereof, it will be apparent to one skilled in the art that various changes and modifications can be made therein without departing from the spirit and scope thereof.

TABLE 1-1

| | | Primers | | | |
|---|---|---|---|---|---|
| | 1+4 | 2+5 | 3+6 | 7+8 | 7+9 |
| 1 Salmonella typhimurium S-1, 56-1 | + | + | + | + | + |
| 2 Salmonella typhimurium S-2, 56-2 | + | + | + | + | + |
| 3 Salmonella typhimurium S-3, 56-3 | + | + | + | + | + |
| 4 Salmonella typhimurium S-4, 56-4 | + | + | + | + | + |
| 5 Salmonella typhimurium S-5, 56-5 | + | + | + | + | + |
| 6 Salmonella typhimurium S-6, 56-7 | + | + | + | + | + |
| 7 Salmonella typhimurium S-7, 56-8 | + | + | + | + | + |
| 8 Salmonella typhimurium S-8, 56-9 | + | + | + | + | + |
| 9 Salmonella typhimurium S-9, 56-11 | + | + | + | + | + |
| 10 Salmonella typhimurium S-10, 56-12 | + | + | + | + | + |
| 11 Salmonella typhimurium S-11, 56-13 | + | + | + | + | + |
| 12 Salmonella typhimurium S-12, 56-17 | + | + | + | + | + |
| 13 Salmonella typhimurium S-13, 56-18 | + | + | + | + | + |
| 14 Salmonella typhimurium S-14, 56-19 | + | + | + | + | + |
| 15 Salmonella typhimurium S-15, 56-20 | + | + | + | + | + |
| 16 Salmonella typhimurium S-16, 56-21 | + | + | + | + | + |
| 17 Salmonella typhimurium S-17, 56-22 | + | + | + | + | + |
| 18 Salmonella typhimurium 5-18, 56-23 | + | + | + | + | + |
| 19 Salmonella typhimurium S-19, 56-25 | + | + | + | + | + |
| 20 Salmonella typhimurium S-20, 56-26 | + | + | + | + | + |
| 21 Salmonella typhimurium S-21, 56-27 | + | + | + | + | + |
| 22 Salmonella typhimurium S-22, 56-30 | + | + | + | + | + |
| 23 Salmonella typhimurium S-23, 56-31 | + | + | + | + | + |
| 24 Salmonella typhimurium S-24, 56-32 | + | + | + | + | + |
| 25 Salmonella havana S-25, 56-44 | + | + | + | + | + |

TABLE 1-2

| | | Primers | | | |
|---|---|---|---|---|---|
| | 1+4 | 2+5 | 3+6 | 7+8 | 7+9 |
| 26 Salmonella oranienberg S-26, 57-1 | + | + | + | + | + |
| 27 Salmonella oranienberg S-27, 57-2 | + | + | + | + | + |
| 28 Salmonella typhimurium S-28, 57-3 | + | + | + | + | + |
| 29 Salmonella typhimurium S-29, 57-4 | + | + | + | + | + |
| 30 Salmonella typhimurium S-30, 57-5 | + | + | + | + | + |
| 31 Salmonella typhimurium S-31, 57-6 | + | + | + | + | + |
| 32 Salmonella typhimurium S-32, 57-7 | + | + | + | + | + |
| 33 Salmonella typhimurium S-33, 57-9 | + | + | + | + | + |
| 34 Salmonella typhimurium S-34, 57-10 | + | + | + | + | + |
| 35 Salmonella typhimurium S-35, 57-11 | + | + | + | + | + |
| 36 Salmonella typhimurium S-36, 57-19 | + | + | + | + | + |
| 37 Salmonella typhimurium S-37, 57-20 | + | + | + | + | + |
| 38 Salmonella london S-38, 58-7 | + | + | + | + | + |
| 39 Salmonella london S-39, 58-8 | + | + | + | + | + |
| 40 Salmonella london S-40, 58-9 | + | + | + | + | + |
| 41 Salmonella senftenberg S-41, 58-27 | + | + | + | + | + |
| 42 Salmonella senftenberg S-42, 58-28 | + | + | + | + | + |
| 43 Salmonella senftenberg S-43, 58-29 | + | + | + | + | + |
| 44 Salmonella blockley S-44, 58-55 | + | + | + | + | + |
| 45 Salmonella blockley S-45, 58-56 | + | + | + | + | + |
| 46 Salmonella blockley S-46, 58-57 | + | + | + | + | + |
| 47 Salmonella agona S-47, 59-1 | + | + | + | + | + |
| 48 Salmonella agona S-48, 59-2 | + | + | + | + | + |
| 49 Salmonella agona S-49, 59-3 | + | + | + | + | + |
| 50 Salmonella infantis S-50, 59-20 | + | + | + | + | + |

TABLE 1-3

| | | Primers | | | |
|---|---|---|---|---|---|
| | 1+4 | 2+5 | 3+6 | 7+8 | 7+9 |
| 51 Salmonella infantis S-51, 59-21 | + | + | + | + | + |
| 52 Salmonella infantis S-52, 59-22 | + | + | + | + | + |
| 53 Salmonella litchfield S-53, 59-25 | + | + | + | + | + |

TABLE 1-3-continued

| | | Primers | | | |
|---|---|---|---|---|---|
| | 1+4 | 2+5 | 3+6 | 7+8 | 7+9 |
| 54 Salmonella typhimurium S-54, 59-26 | + | + | + | + | + |
| 55 Salmonella typhimurium S-55, 59-27 | + | + | + | + | + |
| 56 Salmonella typhimurium S-56, 59-28 | + | + | + | + | + |
| 57 Salmonella enteritidis S-57, 59-36 | + | + | + | + | + |
| 58 Salmonella enteritidis S-58, 59-37 | + | + | + | + | + |
| 59 Salmonella enteritidis S-59, 59-38 | + | + | + | + | + |
| 60 Salmonella typhimurium S-60, 59-54 | + | + | + | + | + |
| 61 Salmonella typhimurium S-61, 59-55 | + | + | + | + | + |
| 62 Salmonella typhimurium S-62, 59-56 | + | + | + | + | + |
| 63 Salmonella typhimurium S-63, 59-57 | + | + | + | + | + |
| 64 Salmonella typhimurium S-64, 59-59 | + | + | + | + | + |
| 65 Salmonella typhimurium S-65, 60-5 | + | + | + | + | + |
| 66 Salmonella typhimurium S-66, 60-6 | + | + | + | + | + |
| 67 Salmonella typhimurium S-67, 60-7 | + | + | + | + | + |
| 68 Salmonella typhimurium S-68, 60-13 | + | + | + | + | + |
| 69 Salmonella typhimurium S-69, 61-1 | + | + | + | + | + |
| 70 Salmonella thompson S-70, 61-2 | + | + | + | + | + |
| 71 Salmonella thompson S-71, 61-3 | + | + | + | + | + |
| 72 Salmonella thompson S-72, 61-4 | + | + | + | + | + |
| 73 Salmonella typhimurium S-73, 61-16 | + | + | + | + | + |
| 74 Salmonella thompson S-74, 61-17 | + | + | + | + | + |
| 75 Salmonella thompson S-75, 61-18 | + | + | + | + | + |

TABLE 1-4

| | | Primers | | | |
|---|---|---|---|---|---|
| | 1+4 | 2+5 | 3+6 | 7+8 | 7+9 |
| 76 Salmonella paratyphi B S-76, 61-19 | + | + | + | + | + |
| 77 Salmonella paratyphi B S-77, 61-20 | + | + | + | + | + |
| 78 Salmonella paratyphi B S-78, 61-21 | + | + | + | + | + |
| 79 Salmonella typhimurium S-79, 62-1 | + | + | + | + | + |
| 80 Salmonella typhimurium S-80, 62-2 | + | + | + | + | + |
| 81 Salmonella typhimurium S-81, 62-3 | + | + | + | + | + |
| 82 Salmonella typhimurium S-82, 62-4 | + | + | + | + | + |
| 83 Salmonella typhimurium S-83, 62-5 | + | + | + | + | + |
| 84 Salmonella typhimurium S-84, 62-6 | + | + | + | + | + |
| 85 Salmonella paratyphi B S-85, 63-1 | + | + | + | + | + |
| 86 Salmonella paratyphi B S-86, 63-2 | + | + | + | + | + |
| 87 Salmonella paratyphi B S-87, 63-3 | + | + | + | + | + |
| 88 Salmonella typhimurium S-88, 63-6 | + | + | + | + | + |
| 89 Salmonella typhimurium S-89, 63-7 | + | + | + | + | + |
| 90 Salmonella typhimurium S-90, 63-8 | + | + | + | + | + |
| 91 Salmonella typhimurium S-91, 63-9 | + | + | + | + | + |
| 92 Salmonella typhimurium S-92, 89-1 | + | + | + | + | + |
| 93 Salmonella typhimurium S-93, 89-2 | + | + | + | + | + |
| 94 Salmonella thompson S-94, 52-3 | + | + | + | + | + |
| 95 Salmonella thompson S-95, 52-4 | + | + | + | + | + |
| 96 Salmonella enteritidis S-96, 53-1 | + | + | + | + | + |
| 97 Salmonella enteritidis S-97, 53-2 | + | + | + | + | + |
| 98 Salmonella thompson S-99, 53-5 | + | + | + | + | + |
| 99 Salmonella thompson S-100, 53-6 | + | + | + | + | + |
| 100 Salmonella thompson S-101, 53-7 | + | + | + | + | + |

TABLE 1-5

| | | Primers | | | |
|---|---|---|---|---|---|
| | 1+4 | 2+5 | 3+6 | 7+8 | 7+9 |
| 101 Salmonella thompson S-102, 53-20 | + | + | + | + | + |
| 102 Salmonella thompson S-103, 53-21 | + | + | + | + | + |
| 103 Salmonella litchfield S-104, 53-22 | + | + | + | + | + |
| 104 Salmonella litchfield S-105, 53-23 | + | + | + | + | + |
| 105 Salmonella litchfield S-106, 53-24 | + | + | + | + | + |
| 106 Salmonella montevideo S-107, 54-4 | + | + | + | + | + |

TABLE 1-5-continued

| | | Primers | | | |
|---|---|---|---|---|---|
| | 1 + 4 | 2 + 5 | 3 + 6 | 7 + 8 | 7 + 9 |
| 107 Salmonella litchfield S-108, 54-5 | + | + | + | + | + |
| 108 Salmonella litchfield S-109, 54-6 | + | + | + | + | + |
| 109 Salmonella litchfield S-110, 55-3 | + | + | + | + | + |
| 110 Salmonella litchfield S-111, 55-4 | + | + | + | + | + |
| 111 Salmonella litchfield S-112, 55-6 | + | + | + | + | + |
| 112 Salmonella litchfield S-113, 55-7 | + | + | + | + | + |
| 113 Salmonella litchfield S-114, 55-8 | + | + | + | + | + |
| 114 Salmonella litchfield S-115, 55-12 | + | + | + | + | + |
| 115 Salmonella litchfield S-116, 55-13 | + | + | + | + | + |
| 116 Salmonella typhimurium IFO 12529 | + | + | + | + | + |
| 117 Salmonella typhimurium IFO 13245 | + | + | + | + | + |
| 118 Salmonella typhimurium IFO 14193 | + | + | + | + | + |
| 119 Salmonella typhimurium IFO 14194 | + | + | + | + | + |
| 120 Salmonella typhimurium IFO 14209 | + | + | + | + | + |
| 121 Salmonella typhimurium IFO 14210 | + | + | + | + | + |
| 122 Salmonella typhimurium IFO 14211 | + | + | + | + | + |
| 123 Salmonella typhimurium IFO 14212 | + | + | + | + | + |
| 124 Salmonella enteritidis IFO 3313 | + | + | + | + | + |
| 125 Salmonella gallinarum IFO 3163 | + | + | + | + | + |

TABLE 1-6

| | | Primers | | | |
|---|---|---|---|---|---|
| | 1 + 4 | 2 + 5 | 3 + 6 | 7 + 8 | 7 + 9 |
| 126 Salmonella blockley NIAH 1197 | + | + | + | + | + |
| 127 Salmonella choleraesus NIAH 1198 | + | + | + | + | + |
| 128 Salmonella derby NIAH 1199 | + | + | + | + | + |
| 129 Salmonella give NIAH 1214 | + | + | + | + | + |
| 130 Salmonella heidelberg NIAH 1216 | + | + | + | + | + |
| 131 Salmonella infantis NIAH 1218 | + | + | + | + | + |
| 132 Salmonella montevideo NIAH 1221 | + | + | + | + | + |
| 133 Salmonella thompson NIAH 1230 | + | + | + | + | + |
| 134 Salmonella bongori ATCC 43975 | + | + | + | + | + |
| 135 Salmonella diarizonae ATCC 43973 | + | + | + | + | + |
| 136 Salmonella houtenae ATCC 43974 | + | + | + | + | + |
| 137 Salmonella indica ATCC 43976 | + | + | + | + | + |
| 138 Salmonella salamae ATCC 43972 | + | + | + | + | + |
| 139 Salmonella abaetetuba ATCC 35640 | + | + | + | + | + |
| 140 Salmonella etterbeck ATCC 19128 | + | + | + | + | + |
| 141 Salmonella harmelen ATCC 15783 | + | + | + | + | + |
| 142 Salmonella heerlen ATCC 15792 | + | + | + | + | + |
| 143 Salmonella hilversum ATCC 15784 | + | + | + | + | + |
| 144 Salmonella hoograven ATCC 15786 | + | + | + | + | + |
| 145 Salmonella houten ATCC 29834 | + | + | + | + | + |
| 146 Salmonella kahla ATCC 17980 | + | + | + | + | + |
| 147 Salmonella kitenge ATCC 19126 | + | + | + | + | + |
| 148 Salmonella maarssen ATCC 15793 | + | + | + | + | + |
| 149 Salmonella maartensdijk ATCC 15790 | + | + | + | + | + |
| 150 Salmonella maastricht ATCC 15789 | + | + | + | + | + |

TABLE 1-7

| | | Primers | | | |
|---|---|---|---|---|---|
| | 1 + 4 | 2 + 5 | 3 + 6 | 7 + 8 | 7 + 9 |
| 151 Salmonella menden ATCC 15992 | + | + | + | + | + |
| 152 Salmonella nigili ATCC 19127 | + | + | + | + | + |
| 153 Salmonella potsdam ATCC 25957 | + | + | + | + | + |
| 154 Salmonella putten ATCC 15787 | + | + | + | + | + |
| 155 Salmonella schalkwijk ATCC 15785 | + | + | + | + | + |
| 156 Salmonella sloterdijk ATCC 15791 | + | + | + | + | + |
| 157 Salmonella vellore ATCC 15611 | + | + | + | + | + |
| 158 Salmonella zwickau ATCC 15805 | + | + | + | + | + |
| 159 Salmonella paratyphi C ATCC 13428 | + | + | + | + | + |

TABLE 1-7-continued

| | | Primers | | | |
|---|---|---|---|---|---|
| | 1 + 4 | 2 + 5 | 3 + 6 | 7 + 8 | 7 + 9 |
| 160 Salmonella paratyphi B ATCC 8759 | + | + | + | + | + |
| 161 Salmonella arizonae ATCC 13314 | + | + | + | + | + |
| 162 Salmonella choleraesuis ATCC 13312 | + | + | + | + | + |
| 163 Salmonella typhimurium ATCC 43971 | + | + | + | + | + |
| 164 Salmonella enteritidis ATCC 13076 | + | + | + | + | + |
| 165 Salmonella newport ATCC 6962 | + | + | + | + | + |
| 166 Salmonella typhimurium ATCC 13311 | + | + | + | + | + |
| 167 Salmonella typhimurium ATCC 19585 | + | + | + | + | + |
| 168 Salmonella arizonae ATCC 29933 | + | + | + | + | + |
| 169 Salmonella diarizonae ATCC 29934 | + | + | + | + | + |
| 170 Salmonella diarizonae ATCC 31241 | + | + | + | + | + |
| 171 Salmonella choleraesuis ATCC 6958 | + | + | + | + | + |
| 172 Salmonella enteritidis ATCC 4931 | + | + | + | + | + |
| 173 Salmonella enteritidis ATCC 31194 | + | + | + | + | + |
| 174 Salmonella gallinarum ATCC 9184 | + | + | + | + | + |

TABLE 2-1

| | | Primers | | | |
|---|---|---|---|---|---|
| | 1 + 4 | 2 + 5 | 3 + 6 | 7 + 8 | 7 + 9 |
| 1 11. Citrobacter freundii ATCC 6979 | − | − | − | − | − |
| 2 12. Citrobacter freundii ATCC 8090 | − | − | − | − | − |
| 3 13. Citrobacter freundii ATCC 8454 | − | − | − | − | − |
| 4 14. Citrobacter freundii ATCC 10053 | − | − | − | − | − |
| 5 15. Citrobacter freundii ATCC 10787 | − | − | − | − | − |
| 6 16. Citrobacter freundii ATCC 11102 | − | − | + | − | − |
| 7 17. Citrobacter freundii ATCC 11811 | − | − | − | − | − |
| 8 18. Citrobacter freundii ATCC 29219 | − | − | − | − | − |
| 9 19. Citrobacter freundii ATCC 29221 | − | − | − | − | − |
| 10 20. Citrobacter freundii ATCC 29222 | + | − | + | − | − |
| 11 21. Citrobacter freundii ATCC 33128 | − | − | − | − | − |
| 12 22. Citrobacter amalonaticus ATCC 25405 | + | − | − | − | − |
| 13 23. Citrobacter amalonaticus ATCC 25406 | − | − | − | − | − |
| 14 24. Citrobacter amalonaticus ATCC 25407 | + | − | − | − | − |
| 15 25. Citrobacter diversus ATCC 27516 | − | − | − | − | − |
| 16 26. Citrobacter diversus ATCC 29223 | − | − | − | − | − |
| 17 27. Citrobacter diversus ATCC 29224 | − | − | − | − | − |
| 18 44. Citrobacter freundii 51 | − | − | − | − | − |
| 19 45. Citrobacter freundii 52 | − | − | − | − | − |
| 20 46. Citrobacter freundii 53 | − | − | − | − | − |
| 21 47. Citrobacter freundii 54 | − | − | − | − | − |
| 22 48. Citrobacter freundii 55 | − | − | − | − | − |
| 23 49. Citrobacter freundii 56 | − | − | − | − | − |
| 24 50. Citrobacter freundii 57 | − | − | − | − | − |
| 25 51. Citrobacter freundii 58 | − | − | − | − | − |

TABLE 2-2

| | | Primers | | | |
|---|---|---|---|---|---|
| | 1 + 4 | 2 + 5 | 3 + 6 | 7 + 8 | 7 + 9 |
| 26 52. Citrobacter freundii 59 | − | − | − | − | − |
| 27 53. Citrobacter freundii 60 | − | − | − | − | − |
| 28 54. Citrobacter freundii 61 | − | − | − | − | − |
| 29 55. Citrobacter freundii 62 | − | − | − | − | − |
| 30 56. Citrobacter freundii 63 | − | − | − | − | − |
| 31 57. Citrobacter freundii 64 | − | − | − | − | − |
| 32 58. Citrobacter freundii 65 | − | − | − | − | − |
| 33 59. Citrobacter freundii 66 | − | − | − | − | − |
| 34 60. Citrobacter freundii 67 | − | − | − | − | − |
| 35 61. Citrobacter freundii 68 | − | − | − | − | − |
| 36 62. Citrobacter freundii 69 | − | − | − | − | − |
| 37 63. Citrobacter freundii 70 | − | − | − | − | − |
| 38 64. Citrobacter freundii 71 | − | − | − | − | − |
| 39 65. Citrobacter freundii 72 | − | − | − | − | − |

TABLE 2-2-continued

| | | Primers | | | |
|---|---|---|---|---|---|
| | 1+4 | 2+5 | 3+6 | 7+8 | 7+9 |
| 66. Citrobacter freundii 73 | − | − | − | − | − |
| 67. Citrobacter freundii 74 | − | − | − | − | − |
| 68. Citrobacter freundii 75 | − | − | − | − | − |
| 69. Citrobacter freundii 76 | − | − | − | − | − |
| 70. Citrobacter freundii 77 | − | − | − | − | − |
| 71. Citrobacter freundii 78 | − | − | − | − | − |
| 72. Citrobacter freundii 79 | − | − | − | − | − |
| 73. Citrobacter freundii 80 | − | − | − | − | − |
| 74. Citrobacter freundii 81 | − | − | − | − | − |
| 75. Citrobacter freundii 82 | − | − | − | − | − |
| 76. Citrobacter freundii 83 | − | − | − | − | − |

TABLE 2-3

| | | Primers | | | |
|---|---|---|---|---|---|
| | 1+4 | 2+5 | 3+6 | 7+8 | 7+9 |
| 77. Citrobacter freundii 84 | − | − | − | − | − |
| 78. Citrobacter freundii 85 | − | − | − | − | − |
| 79. Citrobacter freundii 86 | − | − | − | − | − |
| 80. Citrobacter freundii A Moriyama | − | − | − | − | − |
| 81. Citrobacter freundii B 1-1 | − | − | − | − | − |
| 82. Citrobacter freundii C 2-1 | − | − | − | − | − |
| 83. Citrobacter freundii D KD 44-9 | − | − | − | − | − |
| 84. Citrobacter freundii E Abdominal Lymph (Ozawa) | − | − | − | − | − |
| 85. Citrobacter diversus Nakatsu | − | − | − | − | − |
| 86. Citrobacter amalonaticus KD 29-6 | − | − | − | − | − |
| 1. V. metschnikovii ATCC7708 (205) | − | − | − | − | − |
| 2. V. furnissi ATCC35016 (214) | − | − | − | − | − |
| 3. V. mimicus ATCC33653 (216) | − | − | − | − | − |
| 4. V. mimicus Lab No.1 (217) | − | − | − | − | − |
| 5. V. mimicus Lab No.14 (218) | − | − | − | − | − |
| 6. V. fluvialis 59H-165 (268) | − | − | − | − | − |
| 7. V. fluvialis 61H-79 (269) | − | − | − | − | − |
| 8. V. fluvialis 61H-175 (270) | − | − | − | − | − |
| 9. V. fluvialis 61H-178 (272) | − | − | − | − | − |
| 10. V. furnissi 61H-180 (273) | − | − | − | − | − |
| 11. V. furnissi 61H-212 (274) | − | − | − | − | − |
| 12. V. mimicus 60H-39 (275) | − | − | − | − | − |
| 13. V. fluvialis 58H-128 (280) | − | − | − | − | − |
| 14. V. parahaemolyticus AQ3115 (1) | − | − | − | − | − |
| 15. V. parahaemolyticus AQ3264 (9) | − | − | − | − | − |

TABLE 2-4

| | | Primers | | | |
|---|---|---|---|---|---|
| | 1+4 | 2+5 | 3+6 | 7+8 | 7+9 |
| 16. V. parahaemolyticus AQ3295 (10) | − | − | − | − | − |
| 17. V. parahaemolyticus AQ3362 (15) | − | − | + | − | − |
| 18. V. parahaemolyticus AQ3465 (25) | − | − | − | − | − |
| 19. V. parahaemolyticus AQ3631 (44) | − | − | − | − | − |
| 20. V. parahaemolyticus AQ3635 (45) | − | − | − | − | − |
| 21. V. parahaemolyticus AQ3694 (50) | − | − | − | − | − |
| 22. V. parahaemolyticus AQ3739 (56) | − | − | − | − | − |
| 23. V. parahaemolyticus AQ3740 (57) | − | − | − | − | + |
| 24. V. parahaemolyticus AQ3741 (58) | − | − | − | − | − |
| 25. V. parahaemolyticus AQ3251 (159) | − | − | − | − | − |
| 26. V. parahaemolyticus AQ4037 (220) | − | − | − | − | − |
| 27. V. parahaemolyticus BG-137 (357) | − | − | − | − | − |
| 28. V. parahaemolyticus AT-4 (385) | − | − | − | − | − |

TABLE 2-4-continued

| | | Primers | | | |
|---|---|---|---|---|---|
| | 1+4 | 2+5 | 3+6 | 7+8 | 7+9 |
| 29. V. parahaemolyticus WP-1 | − | − | − | − | − |
| 30. V. cholerae non O1 Lab No.90 (222) | − | − | − | − | − |
| 31. V. cholerae non O1 Lab No.91 (223) | − | − | − | − | − |
| 32. V. cholerae non O1 Lab No.7 (224) | − | − | − | − | − |
| 33. V. cholerae non O1 AQ1254 (225) | − | − | − | − | − |
| 34. V. cholerae non O1 AQ1255 (226) | − | − | − | − | − |
| 35. V. cholerae non O1 AQ1257 (227) | − | − | − | − | − |
| 36. V. cholerae non O1 AQ1259 (228) | − | − | − | − | − |
| 37. V. cholerae non O1 AQ1261 (229) | − | − | − | − | − |
| 38. V. cholerae non O1 AQ1262 (230) | − | − | − | − | − |
| 39. V. cholerae non O1 AQ1266 (231) | − | − | − | − | − |
| 40. V. cholerae non O1 MDO 1(463:Cholera No.) | − | − | − | − | − |

TABLE 2-5

| | | Primers | | | |
|---|---|---|---|---|---|
| | 1+4 | 2+5 | 3+6 | 7+8 | 7+9 |
| 41. V. cholerae non O1 MDO 14 (475) | − | − | − | − | − |
| 42. V. cholerae non O1 MDO 22 (483) | − | − | − | − | − |
| 43. V. cholerae non O1 A1 1837 (490) | − | − | − | − | − |
| 44. V. cholerae non O1 A1 2118 (494) | − | − | − | − | − |
| 45. V. cholerae non O1 MO 1 (527) | − | − | − | − | − |
| 46. V. cholerae non O1 MO 7 (533) | − | − | − | − | − |
| 47. V. cholerae non O1 VO 1 (575) | − | − | − | − | − |
| 48. V. cholerae non O1 VO 11 (585) | − | − | − | − | − |
| 49. V. cholerae non O1 VO 36 (610) | − | − | − | − | − |
| 50. V. cholerae O1 AQ1011A (1) | − | − | − | − | − |
| 51. V. cholerae O1 TT-1 (31) | − | − | − | − | − |
| 52. V. cholerae O1 A-2 (93) | − | − | − | − | − |
| 53. V. cholerae O1 G-1 (120) | − | − | − | − | − |
| 54. V. cholerae O1 J-1 (127) | − | − | − | − | − |
| 55. V. cholerae O1 J-3 (128) | − | − | − | − | − |
| 56. V. cholerae O1 H-1 (129) | − | − | − | − | − |
| 57. V. cholerae O1 Mobara (130) | − | − | − | − | − |
| 58. V. cholerae O1 Otokawa (132) | − | − | − | − | − |
| 59. V. cholerae O1 KL-2 (133) | − | − | − | − | − |
| 60. V. cholerae O1 NAQ 102 (136) | − | − | − | − | − |
| 61. V. cholerae O1 NAQ 134 (168) | − | − | − | − | − |
| 62. V. cholerae O1 TQ-53 (225) | − | − | − | − | − |
| 63. V. cholerae O1 TQ-96 (268) | − | − | − | − | − |
| 64. V. cholerae O1 MM-2 (339) | − | − | − | − | − |
| 65. V. cholerae O1 BT-1 (422) | − | − | − | − | − |

TABLE 2-6

| | | | Primers | | | | |
|---|---|---|---|---|---|---|---|
| | | | 1 + 4 | 2 + 5 | 3 + 6 | 7 + 8 | 7 + 9 |
| 126 | 66. | V. cholerae O1 BT-3 (424) | − | − | − | − | − |
| 127 | 28. | Escherichia coli JCM 1649 | − | − | − | − | − |
| 128 | 29. | Escherichia coli ATCC 23985 | − | − | − | − | − |
| 129 | 30. | Escherichia coli ATCC 31618 | − | − | − | − | − |
| 130 | 31. | Escherichia coli ATCC 43886 | − | − | − | − | − |
| 131 | 32. | Escherichia coli ATCC 43837 | − | − | − | − | − |
| 132 | 33. | Escherichia coli ATCC 43889 | − | − | − | − | − |
| 133 | 34. | Escherichia coli ATCC 43890 | − | − | − | − | − |
| 134 | 35. | Escherichia coli ATCC 43892 | − | − | − | − | − |
| 135 | 36. | Escherichia coli ATCC 43896 | − | − | − | − | − |
| 136 | 75. | Escherichia coli(VTEC) No.1 VT1 | − | − | − | − | + |
| 137 | 76. | Escherichia coli(VTEC) No.2 VT2 | − | − | − | − | + |
| 138 | 77. | Escherichia coli(VTEC) No.3 VT1, VT2 | − | − | − | − | − |
| 139 | 78. | Escherichia coli(VTEC) No.4 VT1, VT2 | − | − | − | − | − |
| 140 | 79. | Escherichia coli(VTEC) No.7 VT1, VT2 | − | − | − | − | − |
| 141 | 80. | Escherichia coli(VTEC) No.12 VT2vp | − | − | − | − | − |
| 142 | 81. | Escherichia coli(VTEC) No.15 VT1, VT2vhb | − | − | − | − | − |
| 143 | 82. | Escherichia coli(VTEC) No.20 VT1, VT2 | − | − | − | − | − |
| 144 | 83. | Escherichia coli(VTEC) No.32 VT1, VT2 | − | − | − | − | + |
| 145 | 84. | Escherichia coli(VTEC) No.42 VT1, VT2vh | − | − | − | − | − |
| 146 | 85. | Escherichia coli(ETEC) No.3 STh | − | − | − | − | − |
| 147 | 86. | Escherichia coli(ETEC) No.8 LT, STh | − | − | − | − | − |
| 148 | 87. | Escherichia coli(ETEC) No.9 LT, STp | − | − | − | − | − |
| 149 | 88. | Escherichia coli(ETEC) No.17 LT | − | − | − | − | − |
| 150 | 89. | Escherichia coli(ETEC) No.47 STp | − | − | − | − | + |

TABLE 2-7

| | | | Primers | | | | |
|---|---|---|---|---|---|---|---|
| | | | 1 + 4 | 2 + 5 | 3 + 6 | 7 + 8 | 7 + 9 |
| 151 | 90. | Escherichia coli(ETEC) No.58 LT, STh | − | − | − | − | − |
| 152 | 91. | Escherichia coli(ETEC) No.67 LT | − | − | − | − | − |
| 153 | 92. | Escherichia coli(ETEC) No.81 STh | − | − | − | − | − |
| 154 | 93. | Escherichia coli(ETEC) No.168 LT, STp | − | − | − | − | − |
| 155 | 94. | Escherichia coli(ETEC) No.196 LT, STp | − | − | − | − | − |
| 156 | 95. | Escherichia coli(EIEC) No.416 | − | − | − | − | + |
| 157 | 96. | Escherichia coli(EIEC) No.417 | − | − | − | − | − |
| 158 | 97. | Escherichia coli(EIEC) No.418 | − | − | − | − | + |
| 159 | 98. | Escherichia coli(EIEC) No.420 | − | − | − | − | − |
| 160 | 99. | Escherichia coli(EIEC) No.422 | − | − | − | − | − |
| 161 | 100. | Escherichia coli(EIEC) No.423 | − | − | − | − | − |
| 162 | 101. | Escherichia coli(EIEC) No.42. | − | − | − | − | − |
| 163 | 102. | Escherichia coli(EIEC) No.427 | − | − | − | − | − |
| 164 | 103. | Escherichia coli(EIEC) No.428 | − | − | − | − | + |
| 165 | 104. | Escherichia coli(EIEC) No.433 | − | − | − | − | − |
| 166 | 72. | Proteus vulgaris ATCC 27972 | − | − | − | − | − |
| 167 | 73. | Proteus mirabilis ATCC 7002 | − | − | − | − | − |
| 168 | 74. | Proteus mirabilis ATCC 8259 | − | − | − | − | − |
| 169 | 75. | Proteus mirabilis ATCC 10005 | − | − | − | − | − |
| 170 | 76. | Proteus mirabilis ATCC 12453 | − | − | − | − | − |
| 171 | 77. | Proteus mirabilis ATCC 15146 | − | − | − | − | − |
| 172 | 78. | Proteus mirabilis ATCC 25933 | − | − | − | − | − |
| 173 | 79. | Proteus mirabilis ATCC 29245 | − | − | − | − | − |
| 174 | 80. | Hafnia alvei JCM 1666 | − | − | − | − | − |
| 175 | 81. | Providencia rettgeri ATCC 25932 | − | − | − | − | − |

TABLE 2-8

| | | | | Primers | | | | |
|---|---|---|---|---|---|---|---|---|
| | | | | 1 + 4 | 2 + 5 | 3 + 6 | 7 + 8 | 7 + 9 |
| 176 | 49. | Klebsiella pneumoniae | ATCC 4209 | − | − | − | − | − |
| 177 | 50. | Klebsiella pneumoniae | ATCC 10031 | − | − | − | − | − |
| 178 | 51. | Klebsiella pneumoniae | ATCC 13882 | − | − | − | − | − |
| 179 | 52. | Klebsiella pneumoniae | ATCC 13883 | − | − | − | − | − |
| 180 | 53. | Klebsiella pneumoniae | ATCC 23357 | − | − | − | − | − |
| 181 | 54. | Klebsiella pneumoniae | ATCC 27736 | − | − | − | − | − |
| 182 | 55. | Klebsiella pneumoniae | ATCC 29995 | − | − | − | − | − |
| 183 | 56. | Klebsiella pneumoniae | ATCC 33495 | − | − | − | − | − |
| 184 | 57. | Klebsiella pneumoniae | ATCC 35555 | − | − | − | − | − |
| 185 | 58. | Klebsiella oxytoca | ATCC 12833 | − | − | − | − | − |
| 186 | 59. | Klebsiella oxytoca | ATCC 13128 | − | − | − | − | − |
| 187 | 60. | Klebsiella oxytoca | ATCC 15764 | − | − | − | − | − |
| 188 | 61. | Klebsiella oxytoca | ATCC 33496 | − | − | − | − | − |
| 189 | 37 | Shigella dysenteriae | ATCC 9361 | − | − | − | − | − |
| 190 | 38 | Shigella dysenteriae | ATCC 29027 | − | − | − | − | − |
| 191 | 39 | Shigella dysenteriae | ATCC 29028 | − | − | − | − | − |
| 192 | 40 | Shigella flexneri | ATCC 9199 | − | − | − | − | − |
| 193 | 41 | Shigella flexneri | ATCC 11836 | − | − | − | − | − |
| 194 | 42 | Shigella flexneri | ATCC 25875 | − | − | − | − | − |
| 195 | 43 | Shigella | ATCC | | | | | |

TABLE 2-8-continued

|   |   |   |   | Primers | | | | |
|---|---|---|---|---|---|---|---|---|
|   |   |   |   | 1+4 | 2+5 | 3+6 | 7+8 | 7+9 |
|   |   | boydii | 8702 |   |   |   |   |   |
| 196 | 44 | Shigella boydii | ATCC 9207 | − | − | − | − | − |
| 197 | 45 | Shigella boydii | ATCC 9210 | − | − | − | − | − |
| 198 | 46 | Shigella sonnei | ATCC 9290 | − | − | − | − | − |
| 199 | 47 | Shigella sonnei | ATCC 11060 | − | − | − | − | − |
| 200 | 48 | Shigella sonnei | ATCC 29029 | − | − | − | − | − |

TABLE 2-9

|   |   |   |   | Primers | | | | |
|---|---|---|---|---|---|---|---|---|
|   |   |   |   | 1+4 | 2+5 | 3+6 | 7+8 | 7+9 |
| 201 | 62. | Yersinia enterocolitica | ATCC 9610 | − | − | − | − | − |
| 202 | 63. | Enterobacter cloacae | JCM 1232 | − | − | − | − | − |
| 203 | 64. | Serratia marcescens | JCM 1239 | − | − | − | − | − |
| 204 | 65. | Serratia liquefaciens | JCM 1245 | − | − | − | − | − |
| 205 | 66. | Edwardsiella tarda | JCM 1656 | − | − | − | − | − |
| 206 | 67. | Morganella morganii | JCM 1672 | − | − | − | − | − |
| 207 | 68. | Providencia reugeri | ATCC 29944 | − | − | − | − | − |
| 208 | 69. | Providencia stuartii | ATCC 29914 | − | − | − | − | + |
| 209 | 70. | Proteus vulgaris | JCM 1668 | − | − | − | − | − |
| 210 | 71. | Proteus mirabilis | ATCC 29906 | − | − | − | − | − |
| 211 | 67. | Shigella dysenteriae | ATCC 11456a | − | − | − | − | − |
| 212 | 68. | Shigella dysenteriae | ATCC 13113 | − | − | − | − | + |
| 213 | 69. | Shigella flexneri | ATCC 9748 | − | − | + | − | − |
| 214 | 70. | Shigella flexneri | ATCC 9204 | − | − | + | − | + |
| 215 | 71. | Shigella boydii | ATCC 8704 | − | − | − | − | + |
| 216 | 72. | Shigella boydii | ATCC 29928 | − | − | − | − | + |
| 217 | 73. | Shigella sonnei | ATCC 29930 | − | − | − | − | + |
| 218 | 74. | Shigella sonnei | ATCC 25931 | − | − | − | − | − |
| 219 | 1. | Yersinia enterocolitica | 1 | − | − | − | − | − |
| 220 | 2. | Yersinia enterocolitica | 2 | − | − | − | − | − |
| 221 | 3. | Yersinia enterocolitica | 3 | − | − | − | − | − |
| 222 | 4. | Yersinia enterocolitica | 4 | − | − | − | − | − |
| 223 | 5. | Yersinia enterocolitica | 5 | − | − | − | − | − |
| 224 | 6. | Yersinia enterocolitica | 6 | − | − | − | − | − |
| 225 | 7. | Yersinia enterocolitica | 7 | − | − | − | − | − |

TABLE 2-10

|   |   |   |   | Primers | | | | |
|---|---|---|---|---|---|---|---|---|
|   |   |   |   | 1+4 | 2+5 | 3+6 | 7+8 | 7+9 |
| 226 | 8. | Yersinia enterocolitica | 8 | − | − | − | − | − |
| 227 | 9. | Yersinia enterocolitica | 9 | − | − | − | − | − |
| 228 | 10. | Yersinia enterocolitica | 10 | − | − | − | − | − |
| 229 | 11. | Yersinia enterocolitica | 11 | − | − | − | − | − |
| 230 | 12. | Yersinia enterocolitica | 12 | − | − | − | − | − |
| 231 | 13. | Yersinia enterocolitica | 13 | − | − | − | − | − |
| 232 | 14. | Yersinia enterocolitica | 14 | − | − | − | − | − |
| 233 | 15. | Yersinia enterocolitica | 15 | − | − | − | − | − |
| 234 | 16. | Yersinia enterocolitica | 16 | − | − | − | − | − |
| 235 | 17. | Yersinia enterocolitica | 17 | − | − | − | − | − |
| 236 | 18. | Yersinia enterocolitica | 18 | − | − | − | − | − |
| 237 | 19. | Yersinia enterocolitica | 19 | − | − | − | − | − |
| 238 | 20. | Yersinia enterocolitica | 20 | − | − | − | − | − |
| 239 | 21. | Yersinia enterocolitica | 21 | − | − | − | − | − |
| 240 | 22. | Yersinia enterocolitica | 22 | − | − | − | − | − |
| 241 | 23. | Yersinia enterocolitica | 23 | − | − | − | − | − |
| 242 | 24. | Yersinia enterocolitica | 24 | − | − | − | − | − |
| 243 | 25. | Yersinia enterocolitica | 25 | − | − | − | − | − |
| 244 | 26. | Yersinia enterocolitica | 26 | − | − | − | − | − |
| 245 | 27. | Yersinia enterocolitica | 27 | − | − | − | − | − |
| 246 | 28. | Yersinia enterocolitica | 28 | − | − | − | − | − |
| 247 | 29. | Yersinia enterocolitica | 29 | − | − | − | − | − |
| 248 | 30. | Yersinia enterocolitica | 30 | − | − | − | − | − |
| 249 | 31. | Klebiella pneumoniae | 1 | − | − | − | − | − |
| 250 | 32. | Klebiella pneumoniae | 2 | − | − | − | − | − |

TABLE 2-11

| | | | | | Primers | | | | |
|---|---|---|---|---|---|---|---|---|---|
| | | | | | 1+4 | 2+5 | 3+6 | 7+8 | 7+9 |
| 251 | 33. | Klebsiella pneumoniae | 3 | | − | − | − | − | − |
| 252 | 34. | Klebsiella pneumoniae | 4 | | − | − | − | − | − |
| 253 | 35. | Klebsiella pneumoniae | 5 | | − | − | − | − | − |
| 254 | 36. | Klebsiella pneumoniae | 6 | KD 29-4 | − | − | − | − | − |
| 255 | 37. | Klebsiella pneumoniae | 7 | KDC 33-8 | − | − | − | − | − |
| 256 | 38. | Klebsiella pneumoniae | 8 | KD 38-3 | − | − | − | − | − |
| 257 | 39. | Klebsiella oxytoca | 1 | KD 14-6 | − | − | − | − | − |
| 258 | 40. | Klebsiella oxytoca | 2 | KD 43-3 | − | − | − | − | − |
| 259 | 41. | Klebsiella ozaenae | 1 | KD 38-1 | − | − | − | − | − |
| 260 | 42. | Klebsiella oxaenae | 2 | Abdominal Lymph (Ozawa) | − | − | − | − | − |
| 261 | 43. | Klebsiella ornithinolytica | | KDB 35-8 | − | − | − | − | − |
| 262 | 1. | Bucillus cereus | | | − | − | − | − | − |
| 263 | 2. | Bucillus subtilis | | | − | − | − | − | − |
| 264 | 3. | Staphylococcus aureus | | | − | − | − | − | − |
| 265 | 4. | Staphylococcus epidermidis | | | − | − | − | − | − |
| 266 | 5. | Clostridium perfringens | | | − | − | − | − | − |
| 267 | 6. | Vibrio cholerae | | | − | − | − | − | − |
| 268 | 7. | Vibrio cholerae type Ogawa | | | − | − | − | − | − |
| 269 | 8. | Vibrio cholerae type Inaba | | | − | − | − | − | − |
| 270 | 9. | Vibrio fluvialis | | | − | − | − | − | − |
| 271 | 10. | Campylobacter jejuni | | | − | − | − | − | − |
| 272 | 11. | Campylobacter coli | | | − | − | − | − | − |
| 273 | 12. | Escherichia coli | | | − | − | − | − | − |
| 274 | 13. | Yersinia enterocolitica | | | − | − | − | − | − |
| 275 | 14. | Shigella dysenteriae | | | − | − | − | − | − |

TABLE 2-12

| | | | Primers | | | | |
|---|---|---|---|---|---|---|---|
| | | | 1+4 | 2+5 | 3+6 | 7+8 | 7+9 |
| 276 | 15. | Shigella flexneri | − | − | − | − | − |
| 277 | 16. | Shigella sonnei | − | − | − | − | − |
| 278 | 17. | Bacteroides fragilis | − | − | − | − | − |
| 279 | 18. | Bacteroides vulgatus | − | − | − | − | − |
| 280 | 19. | Enterococcus faecalis | − | − | − | − | − |
| 281 | 20. | Klebsiella pneumoniae | − | − | − | − | − |
| 282 | 21. | Proteus vulgaris | − | − | − | − | − |
| 283 | 22. | Citrobacter freundii | − | − | − | − | − |
| 284 | 23. | Streptococcus pyogenes | − | − | − | − | − |
| 285 | 24. | Streptococcus pneumoniae | − | − | − | − | − |
| 286 | 25. | Haemophilus influemzae | − | − | − | − | − |
| 287 | 26. | Proteus mirabillis | − | − | − | − | − |
| 288 | 27. | Neisseria gonorrhoeae | − | − | − | − | − |
| 289 | 28. | Neisseria meningitidis | − | − | − | − | − |
| 290 | 29. | Listeria monocytogenes | − | − | − | − | − |
| 291 | 30. | Lactobacilla acidophilus | − | − | − | − | − |
| 292 | 31. | Bifidobacterium adlescentis | − | − | − | − | − |
| 293 | 32. | Fusobacterium nucleatum | − | − | − | − | − |
| 294 | 33. | Propionibacterium aeruginosa | − | − | − | − | − |
| 295 | 34. | Veillonalla atypica | − | − | − | − | − |
| 296 | 35. | Pseudomonas aeruginasa | − | − | − | − | − |
| 297 | 36. | Corynebacterium diphtheriae | − | − | − | − | − |
| 298 | 37. | Peptostreptococcus anaerobius | − | − | − | − | − |
| 299 | 38. | Human placental DNA | − | − | − | − | − |

What is claimed is:

1. A synthetic oligonucleotide consisting of a nucleotide sequence selected from the group consisting of SEQ ID NOS: 1 to 9.

2. A kit for detection of Salmonella species, comprising at least a pair of primers selected from the group consisting of synthetic oligonucleotides of claim 6, a thermostable DNA polymerase, and dNTP solutions.

3. A method for detecting Salmonella species by selectively amplifying a target gene by PCR, comprising
   (1) hybridizing an oligonucleotide primer to a single-stranded target DNA in a specimen and carrying out a primer extension reaction using the single-stranded target DNA as a template to give a primer extension product,
   (2) denaturing the resulting DNA duplex to separate the primer extension product from the template, the primer extension product functioning as another template for another primer,
   (3) repeating a cycle of simultaneous primer extension reaction with two primers, separation of primer extension products from templates, and hybridization of primers to amplify a region of the target DNA, in the steps from (1) to (3), said primers being selected from the group consisting of synthetic oligonucleotides of claim 6, and
   (4) detecting the amplified nucleotide sequence to determine whether enterotoxic bacteria of Salmonella species are present in the specimen.

4. A synthetic oligonucleotide consisting of a fully complementary sequence to the synthetic oligonucleotide of claim 3.

5. The synthetic oligonucleotide according to claim 3, wherein the oligonucleotide is labelled.

6. The synthetic oligonucleotide according to claim 4, wherein the oligonucleotide is labelled.

7. A primer composition comprising a synthetic oligonucleotide of claim 3 and a suitable carrier therefor.

8. A primer composition comprising a synthetic oligonucleotide of claim 4 and a suitable carrier therefor.

9. The primer composition of claim 7, comprising a mixture of oligonucleotides of SEQ ID NOS: 1 and 4.

10. The primer composition of claim 7, comprising a mixture of oligonucleotides of SEQ ID NOS: 2 and 5.

11. The primer composition of claim 7, comprising a mixture of oligonucleotides of SEQ ID NOS: 3 and 6.

12. The primer composition of claim 7, comprising a mixture of oligonucleotides of SEQ ID NOS: 7 and 8.

13. The primer composition of claim 7, comprising a mixture of oligonucleotides of SEQ ID NOS: 7 and 9.

* * * * *